US012797344B2

(12) United States Patent
Hara et al.

(10) Patent No.: US 12,797,344 B2
(45) Date of Patent: Nov. 17, 2026

(54) METHOD FOR TREATING ALZHEIMER'S DISEASE

(71) Applicants: ICHIMARU PHARCOS CO., LTD., Gifu (JP); Hideaki Hara, Gifu (JP)

(72) Inventors: Hideaki Hara, Gifu (JP); Masashi Mikami, Gifu (JP); Hiroyuki Kojima, Gifu (JP); Tatsuji Takahashi, Gifu (JP); Kenichi Ito, Gifu (JP); Iddamalgoda Arunasiri, Gifu (JP)

(73) Assignees: ICHIMARU PHARCOS CO., LTD., Gifu (JP); Hideaki Hara, Gifu (JP)

( * ) Notice: Subject to any disclaimer, the term of this patent is extended or adjusted under 35 U.S.C. 154(b) by 1055 days.

(21) Appl. No.: 17/772,139

(22) PCT Filed: Oct. 20, 2020

(86) PCT No.: PCT/JP2020/039361
§ 371 (c)(1),
(2) Date: Apr. 27, 2022

(87) PCT Pub. No.: WO2021/085232
PCT Pub. Date: May 6, 2021

(65) Prior Publication Data
US 2022/0401377 A1 Dec. 22, 2022

(30) Foreign Application Priority Data
Oct. 28, 2019 (JP) ................................ 2019-195258

(51) Int. Cl.
*A61K 31/047* (2006.01)
*A61K 31/192* (2006.01)
*A61K 36/23* (2006.01)
*A61P 25/28* (2006.01)

(52) U.S. Cl.
CPC .......... *A61K 31/047* (2013.01); *A61K 31/192* (2013.01); *A61K 36/23* (2013.01); *A61P 25/28* (2018.01)

(58) Field of Classification Search
CPC ...... A61K 31/047; A61K 36/23; A61K 31/19; A61K 31/704; C07C 33/048; A61P 25/28; A61P 39/06
See application file for complete search history.

(56) References Cited

FOREIGN PATENT DOCUMENTS

| | | | | |
|---|---|---|---|---|
| CN | 106117015 A | * 11/2016 | | .......... C07C 33/048 |
| JP | 4624263 B2 | 2/2011 | | |
| JP | 2017137296 A | 8/2017 | | |
| WO | 2005065698 A1 | 7/2005 | | |

OTHER PUBLICATIONS

Parums, D. V. Med Sci Monit 2024, 30, e945091, pp. 1-7.*
Definition of prevent, Princeton University "About WordNet." WordNet. Princeton University. 2010. <http://wordnet.princeton. edu> accessed Sep. 18, 2012.*
Athauda et al. Nature Reviews Neurology 2015, 11, 25-40.*
Zarei et al. Surg. Neurol. Int. 2015, 6, 171.*
MD. Sahab Uddin et al., "Nootropic and Anti-Alzheimer's Actions of Medicinal Plants: Molecular Insight into Therapeutic Potential to Alleviate Alzheimer's Neuropathology", Molecular Neurobiology, 2019, vol. 56, p. 4925-4944, 20p.
K. E. Schulte et al., "Polyacetylene aus *Hydrocotyle asiatica* L." Arch. Pharm, 1973, vol. 306, No. 3, pp. 197-209, 13pp.
Wen-Ling Cheng et al., "Inhibitory Effect of Human Breast Cancer Cell Proliferation via p21-Mediated G1 Cell Cycle Arrest by Alariadiol Isolated from Aralia cordata Thunb", Planta Med, 2011, vol. 77, No. 2, pp. 164-168, 2011, http://dx.doi.org/10.1055/s-0030-1250177, 5pp.
Narendra A, Gajbhiye et al., "LC-ES-MS/MS Method for Simultaneous Determination of Triterpenoid Glycosides and Aglycones in *Centella asiatica* L.", Springer, Chromatographia, 2016, vol. 79, No. 11,12, pp. 727-739, 15p.
Mikami et al., "Centella asiatica and Acorus calamus extracts against neuronal cell death. Cytoprotestive action of the product.", Abstract of 138th Annual Meeting of the Pharmaceutical Society of Japan, 2018, 26PA-aml83S, 1pp.
Mikami et al., "Protective effects of Camellia sinensis extracts and asiaticoside against oxidative stress and endoplasmic reticulum stress-induced neuronal damage.", Folia Pharmacological Japonica, 2019, vol. 154, Special issue 135th Kinki subcommittee, 3pp.
International Search Report issued in PCT/JP2020/039361, mailed Dec. 1, 2020. 4pp.
Written Opinion issued in PCT/JP2020/039361, mailed Jan. 12, 2020. 5pp.
Office Action in JP Application No. 2021-553452, mailed Jan. 9, 2024, 13pp.

* cited by examiner

*Primary Examiner* — Irina Neagu
(74) *Attorney, Agent, or Firm* — HAUPTMAN HAM, LLP

(57) ABSTRACT

Provided is a composition useful for preventing and/or treating neurodegenerative disorders such as Alzheimer's disease and Parkinson's disease. The composition is for preventing and/or treating a neurodegenerative disorder, and contains, as an active ingredient, a compound represented by the following formula (I):

(I)

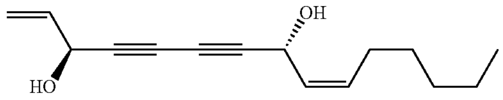

or an isomer thereof, or a salt thereof.

4 Claims, 6 Drawing Sheets

[Fig.1]
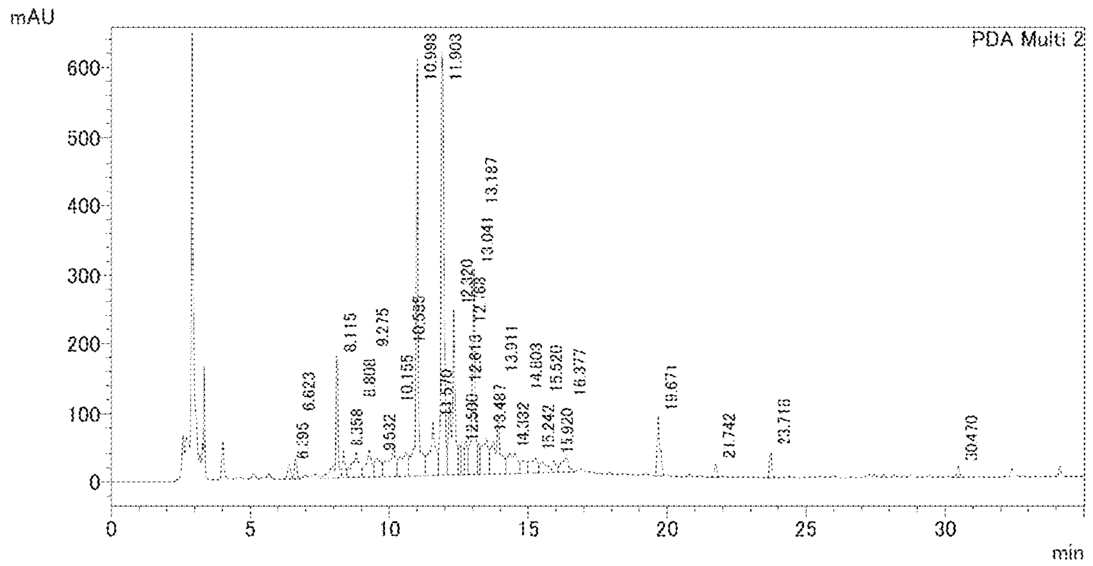
[Fig.2]
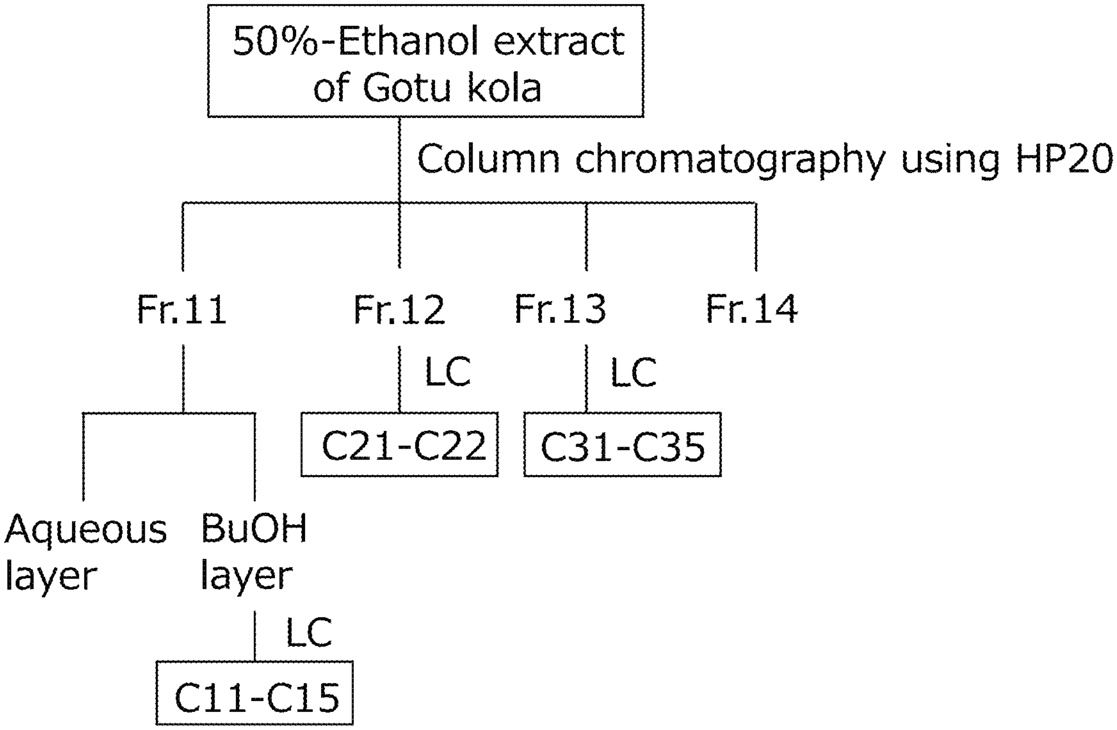

[Fig.3]
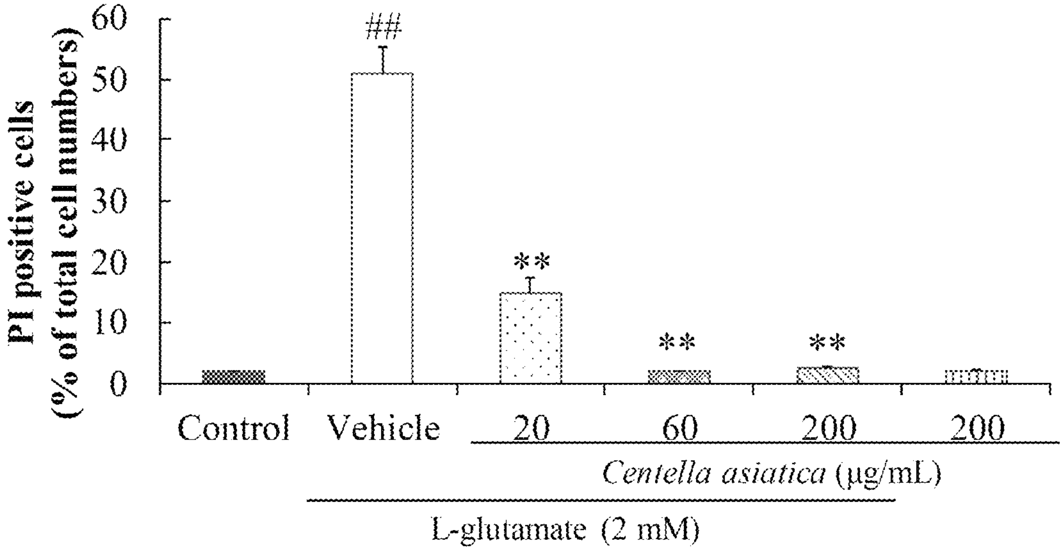
[Fig.4]
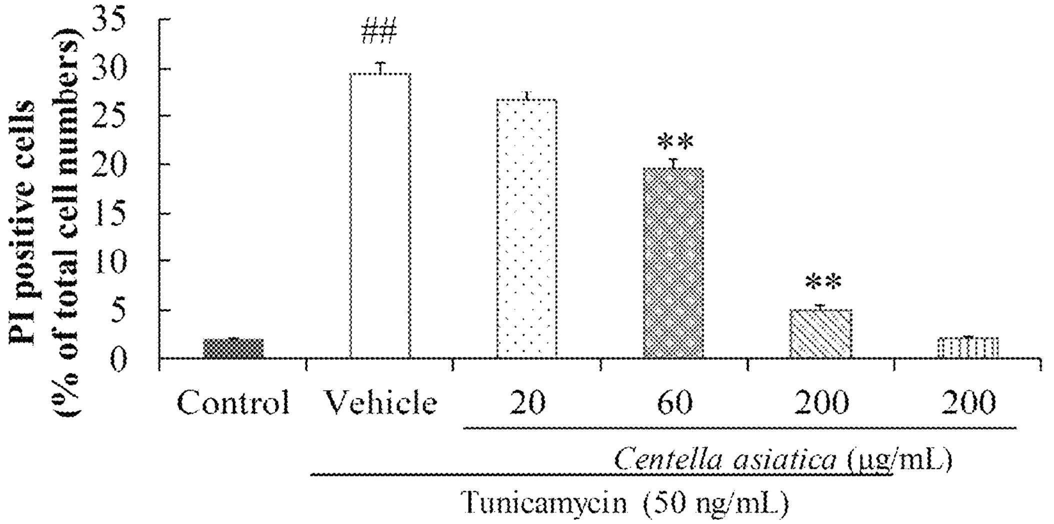

[Fig.5]
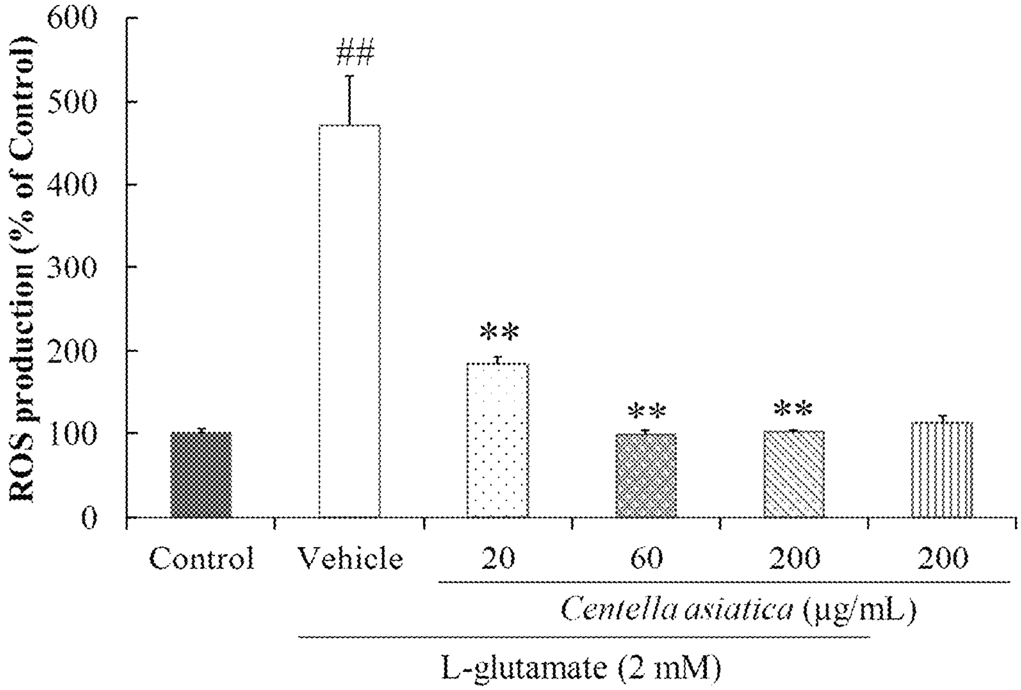
[Fig.6]
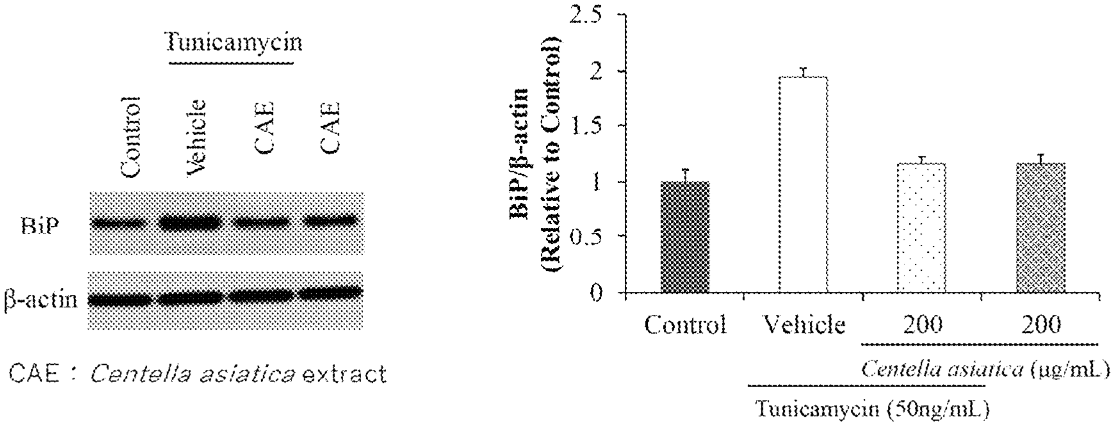

[Fig.7]
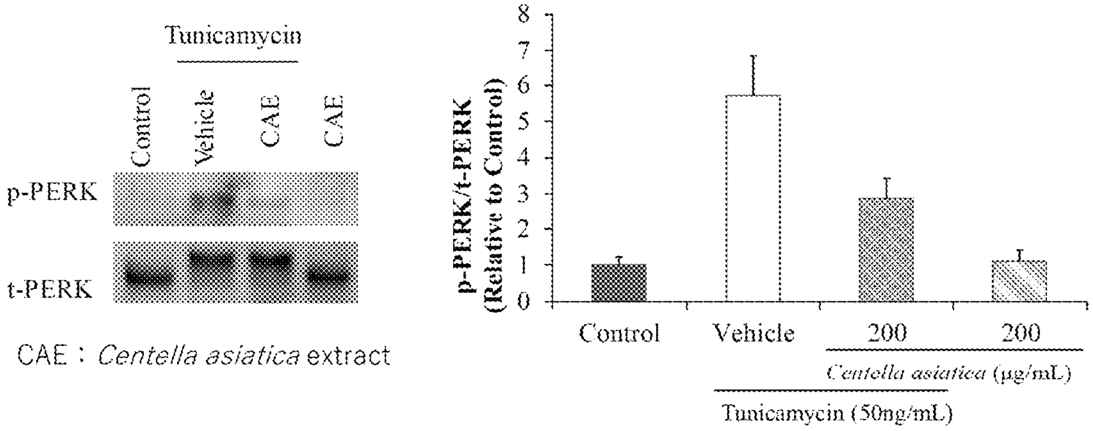
[Fig.8]
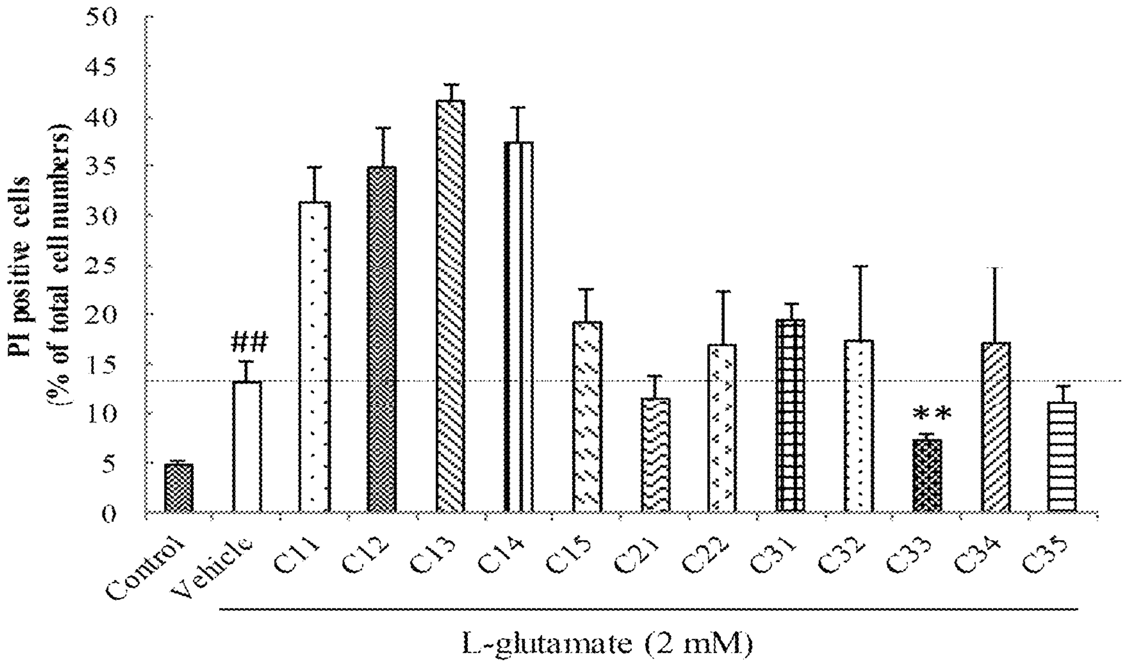

[Fig.9]
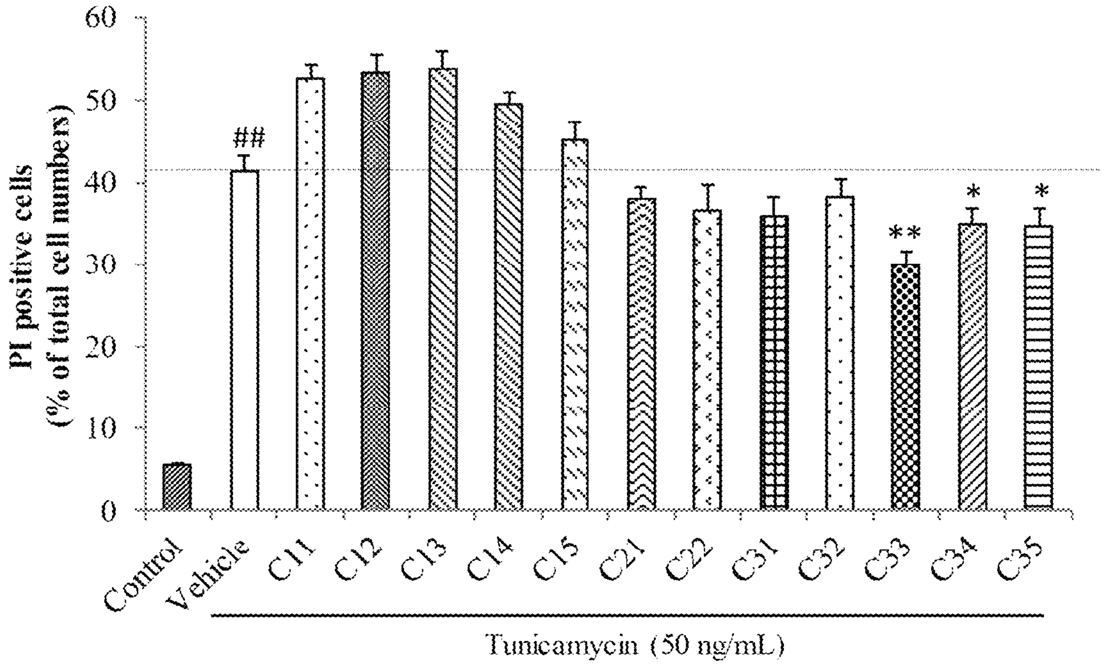
[Fig.10]
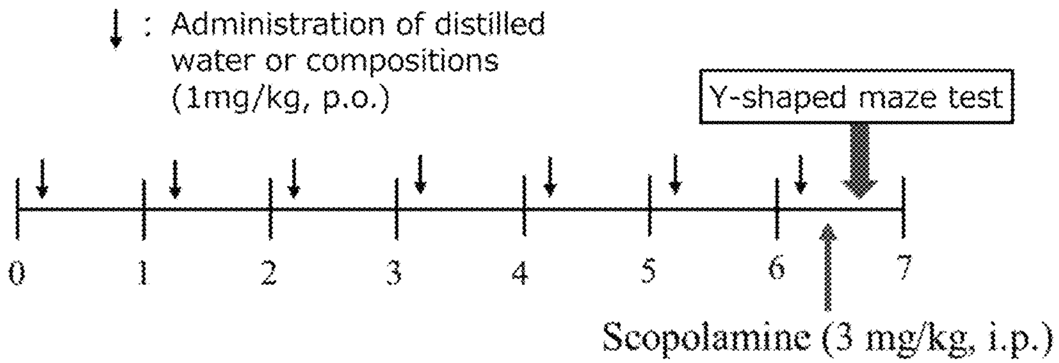

[Fig.11]
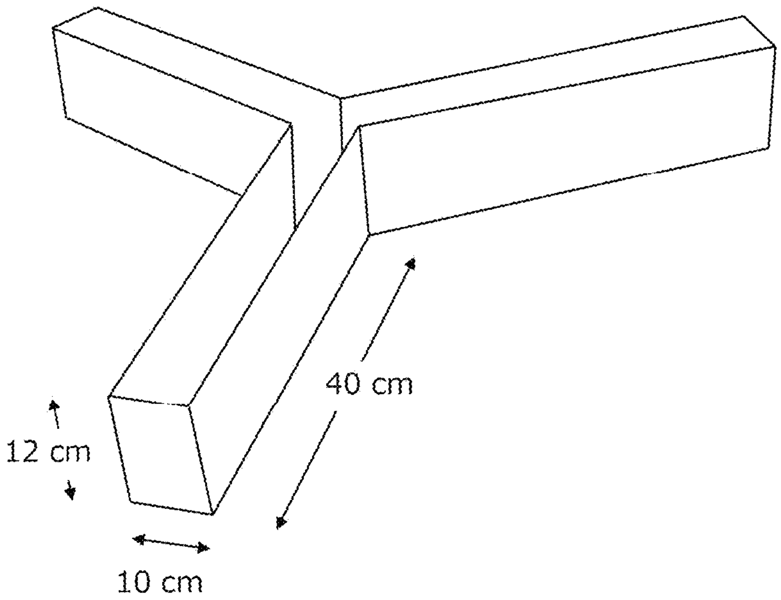

METHOD FOR TREATING ALZHEIMER'S DISEASE

CROSS REFERENCE

This application is a National Stage entry of International Application No. PCT/JP2020/039361, filed on Oct. 20, 2020, which claims priority from Japanese patent Application No. 2019-195258 filed in Japan on Oct. 28, 2019, the entire contents of which are incorporated herein by reference in their entirety.

TECHNICAL FIELD

The present invention relates to a composition for preventing and/or treating neurodegenerative disorders, and more particularly to a composition for preventing and/or treating neurodegenerative disorders containing a certain compound extracted from Gotu kola.

BACKGROUND ART

The number of patients with neurodegenerative disorders, such as Alzheimer's disease, is increasing every year along with the increase in the number of elderly people. Neurodegenerative disorders include conditions in which nerve cells are damaged and functions such as movement and memory are impaired. The problem is that the pathogenesis of these diseases is unclear and there is no curative therapy. A common finding in neurodegenerative disorders is the accumulation of abnormal proteins in the brain. Abnormal proteins accumulated in neurons apparently cause oxidative stress and endoplasmic reticulum (ER) stress. There are also numerous reports implicating oxidative stress and ER stress in the pathogenesis of neurodegenerative disorders.

Gotu kola (*Centella asiatica*; also known as Tsubokusa) has long been used in Ayurveda and is known to have a wide range of effects, including antipyretic, analgesic, anti-inflammatory, and cognitive function improvement. The plant is widely distributed in Japan, Asia, South Africa, and the United States, and is also widely enjoyed as a food.

Patent literature 1 discloses an herbal formulation as a brain tonic, containing Tsubokusa and sesame seeds. Also, patent literature 2 discloses a glucose metabolism activator of astrocytes, a neuronal activator in the brain, a brain function suppressant, a brain function improver, and a brain function enhancer, or an agent for the prevention or amelioration of brain dysfunction comprising as an active ingredient one or more selected from the group consisting of hydrophobic solvent extracts of sugar beet tea, rooibos, and grape.

On the other hand, Araliadiol: 3(S),8(R)-pentadeca-1,9(Z)-diene-4,6-diyne-3,8-diol is a polyacetylene compound isolated from the leaves of *Udo* (botanical name: *Aralia cordata*), and has been reported to arrest the cell cycle and inhibit the proliferation of a human breast cancer cell line (MCF-7). However, the effect of this compound on neurodegenerative disorders is not known (see Non-patent literature 1).

CITATION LIST

Non-Patent Literature

[Non-patent literature 1] Cheng W L et al. (2011) Planta Med; 77: 164-168

Patent Literature

[Patent literature 1] Published examined patent application JP4624263B

[Patent literature 2] Published unexamined patent application JP2017-137296A

SUMMARY OF INVENTION

Technical Problem

It is an object, among others, of the present invention to provide a composition that may be useful in the prevention and/or treatment of neurodegenerative disorders such as Alzheimer's disease, Parkinson's disease, and the like.

Solution to Problem

The inventors analyzed the components of Gotu kola extract using HT22 cells (a cell line derived from hippocampal nerves of mouse brain) and found that a compound of the following structure that inhibits ROS production and reduces endoplasmic reticulum stress (these effects are effective in the prevention and/or treatment of neurodegenerative disorders) and the like.

That is, the invention includes the following embodiments.

(1) A composition for preventing and/or treating a neurodegenerative disorder, the composition comprising, as an active ingredient, a compound represented by the following formula (I):

(I)

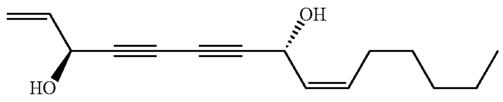

or an isomer thereof, or a salt thereof.

(2) The composition according to (1) further comprising at least one component selected from madecassic acid, asiatic acid and a glycoside thereof.

(3) The composition according to (2), comprising 0.5 to 30 times as much madecassic acid, and 0.25 to 30 times as much asiatic acid relative to the mass of the compound of formula (I).

(4) The composition according to any one of clauses (1) to (3), comprising Gotu kola extract.

(5) The composition according to any one of clauses (1) to (4), which is an inhibitor of a reactive oxygen species.

(6) A food or drink for improving brain function comprising the composition according to any one of clauses (1) to (5).

(7) A pharmaceutical product for improving brain function comprising the composition according to any one of clauses (1) to (5).

Advantageous Effects of Invention

The compositions can be used, for example, for preventing and/or treating neurodegenerative diseases such as Alzheimer's disease and Parkinson's disease.

BRIEF DESCRIPTION OF THE DRAWINGS

FIG. 1 shows a typical HPLC pattern of Gotu kola extract.

FIG. 2 shows a schematic of the method for fractionating active ingredients from Gotu kola extract.

FIG. 3 shows the results of quantification of dead cell rates by propidium iodide (PI) staining and nuclear staining for HT22 cells supplemented with various concentrations of Gotu kola extract and L-glutamic acid (2 mM).

FIG. 4 shows the percentage of dead cells by propidium iodide (PI) staining and nuclear staining for HT22 cells supplemented with various concentrations of Gotu kola extract and tunicamycin (50 ng/mL).

FIG. 5: shows the production of reactive oxygen species (ROS) when oxidative stress is induced by L-glutamic acid in HT22 cells with various concentrations of Gotu kola extract.

FIG. 6 shows the amount of BiP produced by HT22 cells supplemented with various concentrations of Gotu kola extract and induced endoplasmic reticulum stress by tunicamycin.

FIG. 7 shows the amount of phosphorylated PERK protein in HT22 cells supplemented with various concentrations of Gotu kola extract and subjected to endoplasmic reticulum stress induced by tunicamycin.

FIG. 8 shows the results of quantification of dead cell percentage by propidium iodide (PI) staining and nuclear staining for HT22 cells supplemented with L-glutamic acid (2 mM) using the purified fraction of Gotu kola extract.

FIG. 9 shows the quantification of dead cell percentage by propidium iodide (PI) staining and nuclear staining for HT22 cells supplemented with tunicamycin (50 ng/mL) using the purified fraction of Gotu kola extract.

FIG. 10 shows the time series of the administration of distilled water, composition and scopolamine in Test Example 3.

FIG. 11 shows a schematic diagram of the Y-shaped maze device used in Test Example 3.

DESCRIPTION OF EMBODIMENTS

Definition

In this document, neurodegenerative disorder is a general term for diseases in which nerve cells are impaired and brain and other functions such as movement and memory (e.g., brain function) are reduced. Examples include degenerative dementia such as Alzheimer's disease and dementia with Lewy bodies, atrophic lateral sclerosis, Parkinson's disease, progressive supranuclear palsy, Huntington's disease, multiple system atrophy, and spinocerebellar degeneration.

Brain function can be paraphrased as cognitive function. Brain function represents the higher functions of the brain, usually encompassing functions realized by information processing in the brain, such as judgment, calculation, memory, understanding, learning, thinking, and language. Improvement of brain function includes improvement of the above brain functions, i.e., cognitive function.

(Active ingredient)

The composition for preventing and/or treating a neurodegenerative disorder in this embodiment comprises, as an active ingredient, a compound represented by the following formula (I)

(I)

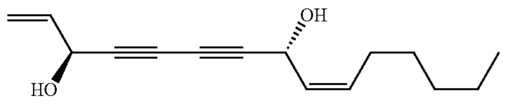

or an isomer of the compound, or a salt thereof. The compound represented by formula (I) contains asymmetric carbon atoms at positions 3 and 8, and the double bond between the carbon atoms at positions 9 and 10 is cis (Z) configuration. Therefore, the active ingredient may be an optical, racemic and/or geometric isomer with respect to these positions. The compound represented by formula (I) is one naturally occurring isomer and has been isolated from an ethanol extract of the leaves of *Udo* (*Aralia cordata*) (see no-patent literature 2). The inventors have found that the compound represented by formula (I), purified from the ethanol extract of Gotu kola by HPLC, is a promising candidate for preventing and/or treating neurodegenerative disorders. Thus, the active ingredient can be produced from medicinal plants such as Gotu kola and *Udo* by organic solvent extraction and column chromatographic purification.

The portion of Gotu kola used in this embodiment is flower, spike, fruit, stem, leaf, petiole, branch, branch leaf, rhizome, root, seed, or whole plant, and homologous species can also be used. It can be extracted with water or an organic solvent (such as ethanol solution), preferably 50% ethanol aqueous solution as the extraction solvent. In this embodiment, an ethanol extract from the whole plant of Gotu kola is preferably used.

The active ingredient of the invention may be in the form of a salt, and when the hydroxy group of the compound represented by formula (I) is moderately acidic, the salt may be, for example, a metal salt such as aluminum; an alkali metal salt such as lithium, sodium or potassium; alkaline earth metal salts such as calcium or magnesium; and an ammonium or substituted ammonium salt, for example, a lower alkyl amine such as triethylamine; a hydroxyalkylamine such as 2-hydroxyethylamine, bis-(2-hydroxyethyl)-amine or tri-(2-hydroxyethyl)-amine; a salt with cycloalkylamine such as bicyclohexylamine; or procaine, dibenzylpiperidine, N-benzyl-β-phenethylamine, and dehydroabietylamine, N,N'-bisdehydroabietylamine, glucamine, N-methylglucamine, or a salt with pyridine-type base such as pyridine, collidine, quinine or quinoline.

(Composition for Preventing and/or Treating Neurodegenerative Disorders)

The amount of the compound represented by the above formula (I) in the composition of the embodiment is not particularly limited, as long as the amount is such that the preventive and/or therapeutic effects of neurodegenerative disorders can be obtained, taking into consideration the form of administration and method of administration. For example, the content of the compound represented by the above formula (I) is 0.1% by mass or more, preferably 0.5, 1, 5, or 10% by mass or more, and less than 90% by mass, preferably 70, 50, 30, or 15% by mass or less, with respect to the total weight of the composition of the present invention. The "% by mass" used herein is synonymous with "% by weight" and means weight/weight (w/w) unless otherwise noted.

The composition of this embodiment may contain other ingredients as long as it contains the compound represented by the above formula (I) as an active ingredient. Other ingredients preferably include triterpene acids such as madecassic acid and asiatic acid and their glycosides. These are components contained in Gotu kola and can be extracted at the same time when the above active ingredients are extracted from Gotu kola, and their structural formulas are shown below.

C34

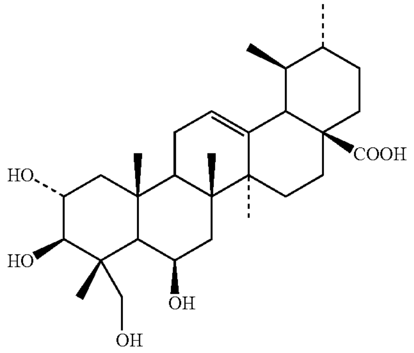

Madecassic Acid

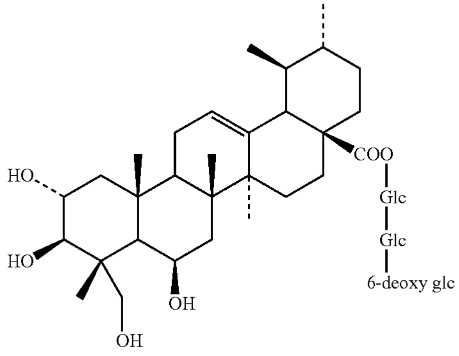

Madecassoside

C35

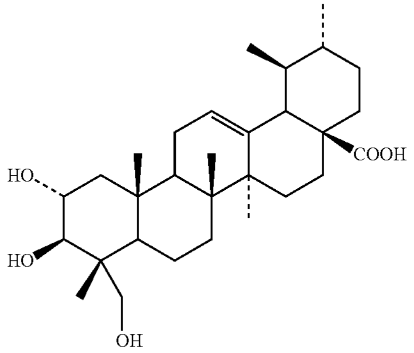

Asiatic acid

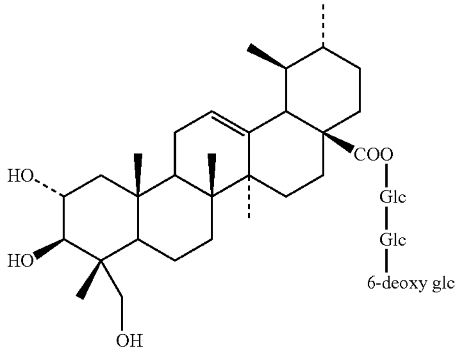

Asiaticoside

According to analysis of the inventors, these triterpene acids and their glycosides also have some degree of neuronal protection. Therefore, it is believed that they exert a synergistic effect when mixed with the active ingredients of this embodiment. As for the blending ratio, the mixture preferably comprises 0.5 to 30 times madecassic acid (more preferably 0.5 to 30 times madecassic acid), and 0.25 to 30 times asiatic acid (more preferably 0.25 to 10 times asiatic acid) in relation to the mass of the compound of formula (I).

(Action and Effect)

This composition may contribute to the improvement of neurodegenerative disorders by inhibiting ROS production and reducing endoplasmic reticulum stress. Neurodegenerative disorders are diseases that impair neurological functions due to damage and loss of specific groups of neurons in the central nervous system. It is known that endoplasmic reticulum stress is involved in the pathogenesis of typical neurodegenerative diseases, such as Alzheimer's disease and Parkinson's disease. A common feature of these diseases is the observed accumulation of degenerative proteins. For example, in Alzheimer's disease, accumulation of amyloid-β extracellularly and tau protein intracellularly is observed. In Parkinson's disease, accumulation of alpha-synuclein, mutant superoxide dismutase in ALS, and huntingtin protein in Huntington's disease are observed. Creutzfeldt-Jakob disease, classified as a prion disease, is caused by the accumulation of abnormal prions. Thus, the proteins that accumulate vary from disease to disease, but it is thought that the accumulation of degenerative proteins causes specific neuronal cell damage and cell death. The endoplasmic reticulum (ER) is responsible for post-translational modification and proper folding of membrane and secretory proteins. When cells are subjected to a variety of internal and external stimulus loads, protein folding in the ER is impaired and defective proteins with defective folding accumulate, resulting in ER stress conditions. When ER stress occurs, the cell attempts to eliminate the defective proteins in order to improve the condition, but excessive ER stress eventually leads to apoptosis of the cell. The production of ROS in the cell is considered one endoplasmic reticulum stress.

(Food or Drink for Improving Brain Function)

Food or drink of this embodiment for improving brain function includes the composition for prevention and/or treatment of the above-mentioned neurodegenerative disorders and is useful for prevention or treatment of diseases or conditions that present disorders of brain function. Such diseases or conditions presenting brain function impairment include, for example, dementia (e.g., senile dementia, Alzheimer's disease, cerebrovascular dementia, post-traumatic dementia, dementia caused by brain tumors, dementia caused by chronic subdural hematoma, dementia caused by normal pressure cerebral edema, dementia after meningitis, and Parkinson's disease), non-dementia cognitive impairment (e.g., mild cognitive impairment (MCI)), and memory or learning impairment (e.g., memory and learning impairment associated with brain developmental disorders). Food or drink of this embodiment for improving brain function includes food with the concept of preventing, improving, or enhancing cognitive function decline and labeled to that effect as necessary, food with functional claims, food for specified health uses, food for the sick, and supplements.

When used as a food, said food may be in the form of various food compositions such as breads, cakes, noodles, confections, jellies, frozen foods, ice cream, dairy products, beverages, etc., as well as the same forms as the orally administered preparations described above (tablets, capsules, syrup, etc.). Foods in various forms can be prepared with the active ingredients of the invention alone or in combination with other food ingredients, solvents, softeners, oils, emulsifiers, preservatives, aromatics, stabilizers, colorants, antioxidants, moisturizers, thickening agents, etc. as appropriate.

(Pharmaceutical Products for Improving Brain Function)

When the compositions of this embodiment are used as pharmaceuticals (including quasi-drugs and the like), they will contain therapeutically effective amounts of the compound represented by formula (I) above and will be administered by any of the dosage forms permitted for drugs that provide similar utility. The therapeutically effective amount of compound will be set according to a number of factors, including the severity of the disease to be treated, the age and relative health of the subject, the potency of the compound used, the route and form of administration, the indication for which administration is directed, and the preference and experience of the physician involved. A person skilled in the art of treating such diseases will be able to determine the therapeutically effective amount of a compound of the invention for a given disease without more experimentation than is necessary and relying on personal knowledge and the disclosure of the present application.

The pharmaceuticals of this embodiment for improving brain function are administered as pharmaceutical formulations, including those suitable for oral (including buccal and sublingual), rectal, intranasal, topical, transpulmonary, transvaginal or parenteral (including intramuscular, intraarterial, intrathecal, subcutaneous and intravenous) administration, or in a form suitable for administration by inhalation or aeration. The preferred method of administration is generally oral, using a convenient daily dosing regimen that can be adjusted according to the degree of distress.

Pharmacologically acceptable carriers may be either solid or liquid. Solid formulations include powders, tablets, rounds, capsules, cachets, suppositories, and dispersible granules. Solid carriers may be one or more substances that can also act as diluents, flavorants, solubilizers, lubricants, suspending agents, binders, preservatives, tablet disintegrants, or encapsulating materials. In powder formulations, the carrier is generally a micronized solid that is a mixture of micronized active ingredient. In tablets, the active ingredient is generally mixed in the appropriate proportions with a carrier having the required binding capacity and formed into the desired shape and size. Powders and tablets preferably contain from about 1 to about 70% of the active compound. Suitable carriers include magnesium carbonate, magnesium stearate, talc, sugar, lactose, pectin, dextrin, starch, gelatin, tragacanth, methylcellulose, sodium carboxymethylcellulose, low melting point waxes, cocoa butter, etc. in a non-limiting manner. The term "formulation" is intended to include formulations of active compounds with encapsulation material as a carrier, providing an encapsulation in which the active ingredient with or without a carrier is surrounded by a carrier associated therewith. Similarly, cachets and trochees are included. Tablets, powders, capsules, rounds, cachets and lozenges can be as solid forms suitable for oral administration.

For example, other forms suitable for oral administration include liquid formulations, including emulsions, syrups, elixirs, aqueous liquids, aqueous suspensions, or solid formulations that are intended to be converted to liquid formulations immediately before use. Emulsions can be prepared in liquid form, e.g., aqueous propylene glycol liquids, or can contain emulsifiers such as lecithin, sorbitan monooleate or acacia. Aqueous liquid formulations can be prepared by dissolving the active ingredients in water and adding appropriate colorants, flavorants, stabilizers and thickeners. Aqueous suspensions can be prepared by dispersing the micronized active ingredient in water with viscous materials such as natural or synthetic gums, resins, methylcellulose, sodium carboxymethylcellulose and other known suspending agents. Solid formulations include liquids, suspensions and emulsions, which can contain, in addition to the active ingredient, colorants, flavorants, stabilizers, buffers, artificial and natural sweeteners, dispersing agents, thickening agents, solubilizers, etc.

Pharmaceuticals of this embodiment for improving brain function can be formulated for parenteral administration (e.g., by injection, e.g., bolus injection or continuous infusion) and can be provided in unit dose form in ampules, pre-filled syringes, small volume infusion, or in multi-dose containers with added preservatives The composition can be in the form of a suspension, liquid or emulsion in an oil-based or water-based vehicle, such as an aqueous polyethylene glycol liquid. Examples of oil-based or non-aqueous carriers, diluents, solvents or vehicles include propylene glycol, polyethylene glycol, vegetable oils (e.g., olive oil), and injectable organic esters (e.g., ethyl oleate), and may contain preservatives, wetting agents, emulsifying or suspending agents, stabilizing agents and/or dispersing agents. Alternatively, the active ingredient may be in powder form obtained by aseptic isolation of sterile solids or by lyophilization from a solution for composition prior to use with an appropriate vehicle, e.g., sterile, pyrogen-free water.

Pharmaceuticals of this embodiment for improving brain function can be formulated for topical administration to the epidermis as an ointment, cream or lotion, or as a transdermal patch. For example, ointments and creams can be formulated with aqueous or oil-based substrates with the addition of appropriate thickening and/or gelling agents. Lotion formulations can be formulated using aqueous or oil-based substrates and will generally also contain one or more emulsifiers, stabilizers, dispersants, suspending agents, thickening agents, or coloring agents. Formulations suitable for topical administration in the oral cavity include lozenges containing the active ingredient in a flavored base, usually sucrose and acacia or tragacanth; flavored tablets containing the active ingredient in an inert base, such as gelatin and glycerin or sucrose and acacia; and Includes mouth rinses containing active ingredients.

Other suitable pharmacological carriers and their formulations can be found in Remington: The Science and Practice of Pharmacy 1995, edited by E. W. Martin, Mack Publishing Company, 19th Edition, Easton, Pa.

EXAMPLE

[Example 1] Preparation of Gotu Kola Extract 6 g each of dried and crushed Gotu kola leaves, stems, or whole plant, was added with 75 mL of 30-90% ethanol, and extracted for 7 days at room temperature with occasional stirring. The resulting extracts were filtered and used as the test sample. The analysis of araliadiol in these test samples was performed under the following conditions.

Column: Mightysil RP-18 GP 250-4.6 (5 μm)

Elution solution: $CH_3CN$: 0.1% phosphoric acid=52:48

Flow rate: 1.0 mL/min

Analysis temperature: 40° C.

Detector: UV 210 nm

The content of araliadiol in Gotu kola extracts varied depending on the region and site of Gotu kola, but the 50% ethanol extract had the highest recovery. Other components such as phenylpropanoids, flavonoids, and triterpenoids were also found to be simultaneously extracted in the 50% ethanol extract of Gotu kola. FIG. 1 shows a typical HPLC pattern of Gotu kola extract. Under these analytical conditions, araliadiol elutes at a retention time of approximately 24 minutes.

[Example 2] Fractionation of Gotu Kola Extract

A schematic of the fractionation method of active ingredients from Gotu kola extract is shown in FIG. 2. The 50% ethanol extract of Gotu kola leaves was first subjected to crude fractionation on a column packed with DIAION HP20 (Mitsubishi Chemical Co., Ltd.). Fraction 11 was extracted with butanol and further subjected to liquid chromatography to fractionate five peak fractions (C11 to C15). Fractions 12 and 13 were similarly subjected to liquid chromatography and obtained the fractions of two peaks (C 21 to C22) and five peaks (C31 to C35), respectively.

The HPLC conditions for the purification of each of the fractions C31-C35 from fraction 13 were as follows:
Column: Develosil ODS-7 20/250 (NW)
Eluent: MeOH:Aq=70:30
Flow rate: 10.0 mL/min
Temperature: Room temperature
Detector: UV 210 nm NMR analysis of the C11 to C35 fractions showed that the component of C33 was found to be araliadiol. In addition, the C21 fraction contained madecassic acid, and the C35 fraction contained asiatic acid as the major component. The measurement data of araliadiol measured with a nuclear magnetic resonance system JEOL (JEOL Corporation) JNM-ECA500 is as follows.

$^{1}$H-NMR (500 MHz, $CDCl_3$) δ: 0.89 (3H, t, J=7.0 Hz, 15-$H_3$), 1.26-1.34 (4H, m, 13, 14-$H_2$), 1.39 (2H, m, 12-$H_2$), 2.10 (2H, brd, J=7.8 Hz, 11-$H_2$), 4.94 (1H, brd, J=5.0 Hz, 3-H), 5.21 (1H, d, J=8.0 Hz, 8-H), 5.26 (1H, d, J=10.0 Hz, 1-Hb), 5.47 (1H, d, J=17.0 Hz, 1-Ha), 5.53 (1H, brd, J=9.0 Hz, 9-H), 5.60 (1H, dt, J=10.5, 7.5 Hz, 10-H), 5.94 (1H, ddd, J=17.0, 10.0, 5.0 Hz, 2-H).

$^{13}$C-NMR (125 MHz, $CDCl_3$) δ: 14.0 (C-15), 22.5 (C-13), 27.7 (C-11), 28.9 (C-12), 31.4 (C-14), 58.6 (C-8), 63.5 (C-3), 68.7 (C-6), 70.3 (C-5), 78.3 (C-4), 79.9 (C-7), 117.3 (C-1), 127.7 (C-9), 134.7 (C-10), 135.8 (C-2).

[Test Example 1] Measurement of the Neuroprotective Effect of Gotu Kola Extract 3000 cells/well in a 96-well plate of mouse hippocampal neuron-derived (HT22) cells were seeded, and after 23 hours, the Gotu kola extract prepared in Example 1 was added at a final concentration of 20-200 μg/mL. One hour after addition, oxidative stress was induced by L-glutamic acid (2 mM) and endoplasmic reticulum stress was induced by tunicamycin (50 ng/mL). The results of those measurements are shown in FIGS. 3 to 7.

FIG. 3 shows the results of propidium iodide (PI) staining and nuclear staining of HT22 cells supplemented with L-glutamic acid (2 mM) to quantify the percentage of dead cells. Approximately 50% of the cells without Gotu kola extract became PI-positive dead cells, while the addition of Gotu kola extract significantly reduced the mortality rate, and the mortality rate was almost the same as the control without L-glutamic acid when the addition of Gotu kola extract at 60 μg/mL and 200 μg/mL, respectively. FIG. 4 shows the percentage of dead cells when tunicamycin (50 ng/mL) was added instead of L-glutamic acid. The addition of Gotu kola extract decreased the dead cell rate in a dose-dependent manner, with the significant differences when the addition of Gotu kola extract at 60 μg/mL and 200 μg/mL.

The effect on oxidative stress was examined by measuring the production of reactive oxygen species (ROS). HT22 cells seeded in a 96 well plates were subjected to oxidative stress induced by L-glutamate. The ROS indicator CM-H2DCFDA was added and absorbance was measured. The results are shown in FIG. 5. The amount of ROS generated by the addition of L-glutamic acid decreased dose-dependently with the addition of Gotu kola extract, to the control level when the addition of Gotu kola extract at 60 μg/mL. Even when Gotu kola extract was added up to 200 μg/mL, there was no difference from the control without L-glutamic acid.

Study on endoplasmic reticulum stress was performed by western blotting. 30,000 cells/well of HT22 cell line inoculated in a 12-well plate, was added with the extract and subjected to the stress. Sampling was then performed and PKR-like endoplasmic reticulum kinase (PERK), Immunoglobulin heavy chain-binding protein (BiP) and Glucose-regulated protein (GRP94) were examined.

The results are shown in FIGS. 6 and 7. BiP, one of the endoplasmic reticulum chaperones, is said to be responsible for the correct folding of incorrectly folded dysfunctional proteins. BiP, which was increased by the effects of endoplasmic reticulum stress induced by tunicamycin, was decreased by the addition of Gotu kola extract (CAE) (FIG. 6). On the other hand, PERK is one of the endoplasmic reticulum stress sensors, which multimerizes after phosphorylation, and by activating downstream signaling factors, causes protein translational arrest and apoptosis. According to the results shown in FIG. 7, the amount of PERK phosphorylated under the influence of endoplasmic reticulum stress induced by tunicamycin was significantly reduced by the addition of the Gotu kola extract.

These results suggest that Gotu kola extract has cytoprotective effects against oxidative stress and endoplasmic reticulum stress, and that the mechanisms involved are inhibition of ROS production and inhibition of endoplasmic reticulum stress generation.

[Test Example 2] Search for Active Ingredients from Purified Gotu Kola Fractions Each fraction of Gotu kola extract fractionated in Example 2 was tested for L-glutamic acid and tunicamycin-induced neuronal damage by the same method as in Test Example 1. In 96-well plates, 3000 cells/well of mouse hippocampal neuron-derived (HT22) cells were inoculated. After 23 hours, each of the C11 to C35 fractions was added to the well at twice concentration contained in the Gotu kola extract. For example, the Gotu kola extract contained 45 μg/mL of C33 fraction. Then, for the C33 fraction, the amount of 90 μg/mL was used, which is twice concentration contained in the Gotu kola extract. One hour after addition, oxidative stress was induced by L-glutamic acid (2 mM) and endoplasmic reticulum stress was induced by tunicamycin (50 ng/mL). Twenty-four hours later, the number of dead cells and total cell numbers were measured by nuclear staining to determine the percentage of dead cells, which was used as an index of neuronal protection. The results are shown in FIGS. 8 and 9.

Among C11 to C35 fractions, the C33 fraction showed significant inhibition of both L-glutamate and tunicamycin-induced cell death. For the other fractions, the C34 and C35 fractions containing triterpenoids significantly inhibited tunicamycin-induced cell death (FIG. 8 and FIG. 9).

[Test Example 3] Confirmation of the Effects of Arariadiol Using a Mouse Model of Memory Impairment The memory-improving effect of araliadiol was confirmed by administering (orally by sonde) a composition containing arariadiol (a compound shown in Formula I) to a mouse model of memory impairment.

Experimental methods are described below. The following groups of ICR mice (male, 7 weeks old/purchased from SLC Japan) were established. The mice in each group, except for the untreated group, were treated with the composition orally administered by sonde and scopolamine administered intraperitoneally (i.p.). The composition contains a predetermined amount of araliadiol in distilled water. Scopolamine was administered at a dose of 3 mg per kg of mice to cause memory impairment in mice. FIG. 10 shows the time series of the administration of distilled water, the composition, and scopolamine. For groups other than the untreated group, distilled water or the composition was administered daily from day 0 to day 6 (seven doses of the composition), with day 0 being the first day of administration of distilled water or the composition. On the 7th day, all groups of mice were tested in a Y-shaped maze test. Scopolamine was administered to all groups of mice except the untreated group 30 minutes before the start of the Y-shaped maze test.

Untreated group: 15 ICR mice that were treated with distilled water containing no araliadiol, but not with scopolamine.

Control group: 16 ICR mice were treated with distilled water containing no araliadiol and scopolamine.

Araliadiol 1 mg/kg group: 16 ICR mice were treated with a composition containing araliadiol (1 mg of araliadiol per 1 kg of mouse body weight per day: 1 mg/kg/day) and scopolamine.

Araliadiol 10 mg/ml group: A group of 16 ICR mice that received a composition containing araliadiol (10 mg of araliadiol per kg of mouse body weight per day: 10 mg/kg/day) and a dose of SCOPE.

The Y-shaped maze device shown in FIG. 11 (made of gray acrylic: 40 cm long×10 cm wide×12 cm high) was used to conduct the Y-shaped maze test. In the Y-shaped maze test, mice were allowed to explore in the device, and the spontaneous alternations observed during the exploratory behavior were evaluated as short-term memory. The mice were placed at the tip of one of the three arms of the Y-shaped maze, allowed to explore freely in the maze for 8 minutes, and the arms they entered were recorded in order. The number of times for the mouse to enter each arm (total number of arm entries) and the number of combinations of consecutive entries into three different arms (number of alternation behaviors) were examined during the measurement period (8 minutes). The alternation behavior (%) was calculated from the following formula and used as an index of short-term memory.

$$\text{Alternating behavior (\%)} = \text{number of alternating actions} / (\text{total number of arm entries} - 2) \times 100$$

Results are shown in Table 1. Compared to the control group, the araliadiol-treated groups (araliadiol 1 mg/kg and araliadiol 10 mg/kg group) showed an increase in the rate of alternation behavior (a trend toward memory improvement). The 10 mg/kg araliadiol group showed a significant (Dunnett's test, $p<0.05$), indicating an improvement in the rate of alternating behavior.

TABLE 1

| | Untreated group | Control group | Araliadiol 1 mg/kg group | Araliadiol 10 mg/kg group |
|---|---|---|---|---|
| Alternating behavior (%) | 64.38 | 48.68 | 50.87 | 53.18(*) |

(*)$p < 0.05$ versus Control (Dunnett's test)

The embodiment of the present invention (including examples) has been described above with reference to the drawings. The specific configurations of the present invention are not limited thereto, and any design changes, etc., are included in the present invention to the extent that they do not depart from the gist of the invention.

The invention claimed is:

1. A method for treating Alzheimer's disease in a subject in need thereof, comprising administering to the subject a composition containing an effective amount of a compound of formula (I):

(I)

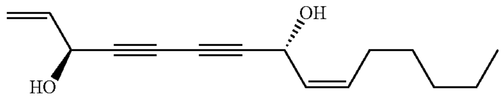

or a pharmaceutically acceptable salt thereof, as an only therapeutic agent.

2. The method according to claim 1, wherein the compound of formula (I) is obtained from Gotu kola extract.

3. The method according to claim 1, wherein the composition is a food or drink composition.

4. The method according to claim 1, wherein the composition is a pharmaceutical product.

* * * * *